(12) United States Patent
Sahner et al.

(10) Patent No.: US 11,564,592 B2
(45) Date of Patent: Jan. 31, 2023

(54) DEVICE, SYSTEM, AND METHOD FOR PROVIDING A CALIBRATION FLUID FOR THE CALIBRATION AND QUALITY CONTROL OF A RESPIRATORY GAS ANALYSIS DEVICE

(71) Applicant: Robert Bosch GmbH, Stuttgart (DE)

(72) Inventors: Kathy Sahner, Mannheim (DE); Kathrin Scheck, Waiblingen (DE); Heike Jank, Kernen im Remstal (DE); Sonja Riehl, Waiblingen (DE)

(73) Assignee: Robert Bosch GmbH, Stuttgart (DE)

( * ) Notice: Subject to any disclaimer, the term of this patent is extended or adjusted under 35 U.S.C. 154(b) by 686 days.

(21) Appl. No.: 16/608,128

(22) PCT Filed: Apr. 26, 2018

(86) PCT No.: PCT/EP2018/060739
§ 371 (c)(1),
(2) Date: Oct. 24, 2019

(87) PCT Pub. No.: WO2018/202543
PCT Pub. Date: Nov. 8, 2018

(65) Prior Publication Data
US 2020/0129090 A1    Apr. 30, 2020

(30) Foreign Application Priority Data
May 3, 2017   (DE) ..................... 10 2017 207 429.9

(51) Int. Cl.
*A61B 5/08*      (2006.01)
*G01N 33/00*    (2006.01)
*G01N 33/497*  (2006.01)

(52) U.S. Cl.
CPC ......... *A61B 5/082* (2013.01); *G01N 33/0006* (2013.01); *A61B 2560/0214* (2013.01);
(Continued)

(58) Field of Classification Search
None
See application file for complete search history.

(56) References Cited

U.S. PATENT DOCUMENTS 6,632,674 B1    10/2003  Warburton
2005/0262924 A1  12/2005  Wood et al.
(Continued)

FOREIGN PATENT DOCUMENTS

CN    102506931 A    6/2012
DE    36 42 609 C1   7/1987
(Continued)

OTHER PUBLICATIONS

International Search Report corresponding to PCT Application No. PCT/EP2018/060739, dated Jul. 20, 2018 (German and English language document) (7 pages).

*Primary Examiner* — Jay B Shah
(74) *Attorney, Agent, or Firm* — Maginot, Moore & Beck, LLP

(57) ABSTRACT

A device for providing a calibration fluid, in particular a nitrogen oxide, for calibrating a respiratory gas analysis device, includes a first interface for connecting a chamber of the device to a measurement path of the respiratory gas analysis device, a first opening for introducing a reactant carrier with a first reactant into the chamber, and a contact element. The contact element is arranged in the chamber relative to the first opening such that when the reactant carrier is introduced, a contact of the contact element with the reactant carrier is facilitated in order to trigger a chemical reaction of the first reactant so as to generate the calibration fluid. The disclosure further relates to a system, a reactant carrier, and a method for providing a calibration fluid for calibrating a respiratory gas analysis device.

17 Claims, 4 Drawing Sheets

(52) U.S. Cl.
CPC .............. *A61B 2560/0223* (2013.01); *G01N 2033/4975* (2013.01)

(56) References Cited

U.S. PATENT DOCUMENTS

| | | |
|---|---|---|
| 2006/0266097 A1 | 11/2006 | Eickhoff |
| 2006/0266098 A1 | 11/2006 | Eickhoff et al. |
| 2008/0156071 A1 | 7/2008 | Tobias |
| 2008/0156074 A1 | 7/2008 | Tobias |
| 2010/0223975 A1 | 9/2010 | Lueck et al. |

FOREIGN PATENT DOCUMENTS

| | | |
|---|---|---|
| DE | 101 37 565 A1 | 3/2003 |
| DE | 10 2009 056 338 A1 | 6/2011 |
| DE | 10 2014 108 109 A1 | 12/2015 |
| EP | 1 384 069 B1 | 6/2006 |
| EP | 1 992 945 A2 | 11/2008 |

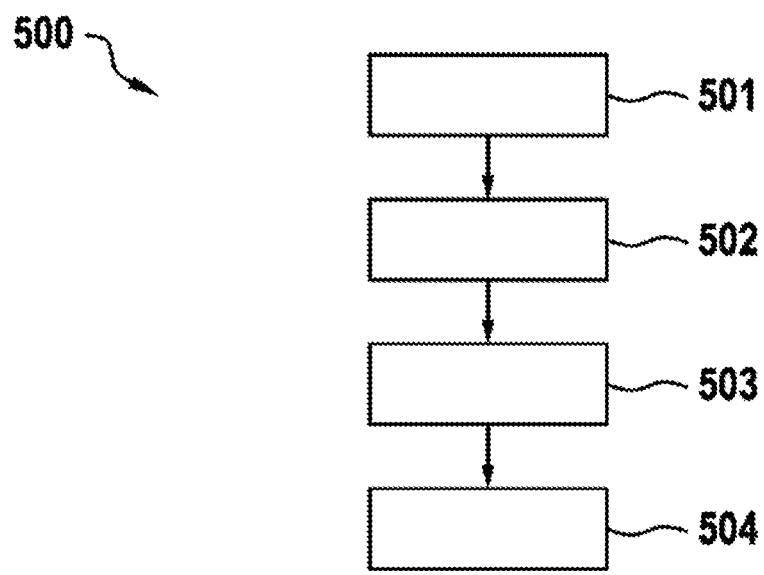

ated by the first reactant carrier of
DEVICE, SYSTEM, AND METHOD FOR PROVIDING A CALIBRATION FLUID FOR THE CALIBRATION AND QUALITY CONTROL OF A RESPIRATORY GAS ANALYSIS DEVICE This application is a 35 U.S.C. § 371 National Stage Application of PCT/EP2018/060739, filed on Apr. 26, 2018, which claims the benefit of priority to Serial No. DE 10 2017 207 429.9, filed on May 3, 2017 in Germany, the disclosures of which are incorporated herein by reference in their entirety.

BACKGROUND

By means of quantitative measurements of analytes in exhaled air, certain respiratory diseases can be detected and monitored. For example, by determining the nitrogen monoxide concentration in exhaled air, the degree of inflammation of the lungs in the case of asthma can be estimated.

The determination of the nitrogen monoxide concentration can be carried out using a device disclosed in EP 1384069 B1 by converting nitrogen monoxide to nitrogen dioxide and then measuring the nitrogen dioxide concentration by means of a field-effect-transistor-based gas sensor in the device. To that end, the gas sensor has on its gate electrode a sensitive layer for the accumulation of nitrogen dioxide. In order to regenerate the gas sensor, and in particular the sensitive layer, after a measurement, flushing of the sensitive layer with heating is necessary. However, it is thereby generally not possible to completely remove nitrogen dioxide which has accumulated on the sensitive layer and other species which interfere with the measurement.

SUMMARY

Against this background, the disclosure relates to a device, a system and a method for providing a calibration fluid, in particular a nitrogen oxide, for the calibration of a respiratory gas analysis device.

The device for providing a calibration fluid comprises a first interface for connecting a chamber of the device to a measurement path of the respiratory gas analysis device. The device further comprises a first opening for the introduction of a reactant carrier having a first reactant into the chamber, and a contact element. The contact element is so arranged in the chamber relative to the first opening that, when the reactant carrier is introduced, contact of the contact element with the reactant carrier for initiating a chemical reaction of the first reactant to produce the calibration fluid is made possible.

A calibration fluid is to be understood as being in particular a gas or a gas mixture of a specified composition so that, by using the calibration fluid, well-defined calibration of the respiratory gas analysis device is possible. The calibration fluid can comprise nitrogen oxides, in particular nitrogen monoxide and/or nitrogen dioxide. A respiratory gas analysis device is to be understood as being in particular a device for measuring analytes in exhaled air, also called an instrument for respiratory gas analysis, for example a device disclosed in EP 1384069 B1 for measuring nitrogen monoxide in exhaled air on the basis of a conversion of nitrogen monoxide to nitrogen dioxide and measurement of the nitrogen dioxide concentration. The first interface can in particular be a connection for the respiratory gas analysis device, for example part of an in particular interlocking connection with the respiratory gas analysis device, for example part of a clip connection or part of a plug-in connection. The first interface can comprise a closable opening between the chamber of the device and a region outside the device. The chamber is in particular a cuboid-shaped, for example cube-shaped, or cylinder-shaped cavity in the device, wherein the volume of the cavity is specified for a well-defined volume of the calibration fluid, in particular calibration gas, to be produced in the chamber. The first opening can in particular be in the form of a slot for the introduction of a reactant carrier in strip form. The contact element is to be understood as being in particular a structure arranged in the chamber. In particular, the contact element is configured to initiate the chemical reaction with the first reactant for producing the calibration fluid on introduction of the reactant carrier via the first opening.

The device according to the disclosure has the advantage that the respiratory gas analysis device can be re-calibrated in a simple manner after previous use. In addition, the effectiveness of a previous flushing of the gas sensor of the respiratory gas analysis device can advantageously be checked. Via the specification of the chemical reaction for producing the calibration fluid and the amounts of reactants involved therein, and via the well-defined volume of the chamber of the device, a well-defined concentration of calibration fluid for the calibration measurement can be supplied to the respiratory gas analysis device. The disclosure thus advantageously allows the measured concentration to be compared in a simple manner with the specified concentration in order to check the measurement accuracy. As a result, a quality control of the device can also be carried out in a simple manner, in particular when the device is used in the field. It is further advantageous that, for providing the calibration fluid, it is not necessary to provide a connection to a fluid line or to a storage container for fluid, in particular a connection to a gas line or a pressurized gas bottle. In particular because no storage container for fluid is required and the calibration fluid can be produced only when it is actually needed, the device can advantageously be compact and space-saving in construction. Producing the calibration fluid only when it is actually needed additionally has the advantage that the calibration fluid can always be freshly produced and thus generally has a higher quality and/or stability compared with a stored calibration fluid.

Preferably, the contact element comprises a structure, in particular a projection, for contacting the reactant carrier which has been introduced. The structure can thereby be so arranged and configured relative to the first opening that it limits the introduction of the reactant carrier into the chamber to a specific degree. The contact element, on account of the barrier to further introduction, thus advantageously also gives the user haptic feedback, transmitted via the reactant carrier, when the reactant carrier touches the projection of the contact element. The structure can thereby be integrally formed with a wall of the chamber. In particular, the structure can be configured for fixing the reactant carrier in the chamber. For example, the structure can comprise one or more projections, recesses and/or walls which enclose the reactant carrier at least in part and thereby prevent a movement in particular transversely to the insertion direction into the chamber. For example, the structure comprises an at least partially U-shaped enclosure for the reactant carrier which has been introduced.

In a particularly advantageous further development of the disclosure, the device comprises a movable piston or plunger for displacing via the first interface the calibration fluid which has been produced. Preferably, the piston or plunger is movable along a longitudinal axis in the direction towards the first interface, wherein the piston or plunger preferably has a surface which completely fills a cross-sectional surface of the preferably cuboid-shaped or cylinder-shaped chamber transversely to the longitudinal axis. This allows a well-defined displacement of calibration fluid situated between the surface of the piston or plunger and the cross-sectional surface through an opening of the first interface into the measurement path of the respiratory gas analysis device connected to the first interface.

The device can comprise a slider which is operable from outside the device and which is connected to the piston or plunger for moving the piston or plunger. Alternatively or in addition, in a particular embodiment of the disclosure the device comprises a drive for moving the piston or plunger. The drive can in particular be an electric motor which is connected to an electrical controller of the device. This has the advantage that a user of the device can effect a displacement of the calibration fluid out of the chamber into the respiratory gas analysis device without applying force.

In a particularly advantageous further development of the disclosure, the contact element comprises a heater for heating the first reactant. The heating can advantageously serve to initiate a chemical reaction of the first reactant for producing the calibration fluid, in particular a calibration gas, for example via oxidation of the first reactant. The heater can advantageously be adapted to heat to a specified reaction temperature in order to provide a defined temperature for the first reactant.

According to an advantageous embodiment of the disclosure, the contact element comprises an electrical conducting contact surface for electrical contact with the reactant carrier which has been introduced. The device can be adapted to detect, via the electrical contact, the presence of a reactant carrier which has been introduced into the device. The device can further be adapted, in the case of such a detection, to effect an activation for producing the calibration gas, for example via an activation of the heater of the contact element. For example, the contact element can be adapted, via the electrical contacting of the reactant carrier with the contact surface of the contact element, to close a current circuit for supplying current to the heater. This has the advantage that heating of the reactant carrier can take place immediately after it has been inserted into the first opening. Furthermore, the device, in particular the contact element, can comprise a temperature sensor for determining the temperature in the chamber and/or for determining the temperature of the reactant carrier. Preferably, the contact element is thereby also in the form of a temperature sensor, in particular in the form of a resistance thermometer. The device can thereby be adapted to control a regulation of the heater via the determination of the temperature.

In a further advantageous embodiment of the disclosure, the contact element comprises a second reactant. This is advantageous in particular when the production of the calibration fluid is to take place via a reaction of two reactants. The first reactant is introduced via the reactant carrier and brought into contact with the second reactant previously deposited on the contact element. If necessary for the chemical reaction, the first and/or second reactant can be brought to a specified temperature for starting the chemical reaction via the heater, which is preferably present, of the device. If three reactants are required for the chemical reaction for producing the calibration fluid, two of the reactants, preferably already mixed with one another, can be previously deposited either on the reactant carrier or on the contact element, and the third reactant can be previously deposited on the contact element or on the reactant carrier.

In a further advantageous embodiment of the disclosure, the contact element comprises an opening element, in particular a pin, a needle, a projection or a plunger, for opening a container of the reactant carrier in order to release the first and/or second reactant from the container. This is advantageous in particular when reactants for producing the calibration fluid are in liquid form. The opening element can preferably be so oriented relative to the first opening that, when the reactant carrier is introduced into the chamber via the first opening, the opening element effects opening of the container. In other words, when the user of the device inserts the reactant carrier into the first opening, he also effects opening of the container at the same time. In the case of a needle or a pin, the needle or the pin can for that purpose extend in the direction towards the first opening. In the case of a plunger or projection, the plunger or projection can be so arranged that the container of the reactant carrier breaks open under the action of the force of the reactant carrier against the projection or plunger.

In an advantageous further development of the disclosure, the device can be configured as part of a charging device or charging station for the respiratory gas analysis device, in particular for electrically charging an energy store of the respiratory gas analysis device. This has the advantage that the two functions of charging and calibration can be accommodated compactly in a common device. The disclosure accordingly also provides a charging device, in particular a charging station, for a respiratory gas analysis device comprising a device according to the invention disclosure.

The disclosure also provides a reactant carrier for the chemical production of a calibration fluid in a device according to the disclosure for the calibration of a respiratory gas analysis device, wherein the reactant carrier is in particular in strip form and comprises a first reactant and a heater, in particular a microsystem heater, wherein the heater is arranged beneath the first reactant. The reactant carrier has the advantage that the heater and the first reactant arranged next to it can be provided together for the device according to the disclosure. Furthermore, the reactant carrier can be used multiple times by applying new reactants. Moreover, a heater does not have to be provided in the device according to the disclosure and, depending on the reactants, a reactant carrier with or without a heater can be introduced into the device.

Preferably, the reactant carrier comprises an electrical contact surface which is connected to the heater. The reactant carrier can be adapted to start the heater when electrical contact is made via the contact surface, that is to say when an electric potential or a current is applied via the contact surface. Preferably, electrical contact can take place via the above-described electrical contact surface of the contact element.

As stated above, the disclosure additionally provides a system for providing a calibration fluid, in particular a nitrogen oxide, for the calibration of a respiratory gas analysis device. The system comprises a device according to the disclosure or a charging device according to the disclosure for the respiratory gas analysis device comprising the device according to the disclosure. The system further comprises a reactant carrier, in particular the reactant carrier according to the disclosure, having a first reactant for the chemical production of the calibration fluid.

The disclosure further provides a method for calibrating a respiratory gas analysis device. In a first step, the respiratory gas analysis device is connected to a device for providing a calibration fluid, wherein the connection of the respiratory gas analysis device to the device takes place via a first interface of the device. In a second step, a reactant carrier having a first reactant is introduced into a chamber of the device. Alternatively, the second step can also take place before the first step. In a third step, the calibration fluid, in particular comprising one or more different nitrogen oxides, can be produced in the chamber via a chemical reaction of the first reactant. In a fourth step, the calibration fluid is introduced into a measurement path of the respiratory gas analysis device for the calibration of the respiratory gas analysis device.

With regard to the advantages of the method according to the disclosure and the following advantageous further developments and embodiments, reference is also made to the corresponding further developments and embodiments of the device according to the invention disclosure mentioned above.

In a particularly advantageous embodiment of the method, the introduction of the calibration fluid into the measurement path is assisted by suction by means of a pump of the respiratory gas analysis device.

According to an advantageous further development of the method, at least a portion of the reactant carrier which comprises the first reactant is heated to a reaction temperature via a heater of the device.

In a further particularly advantageous embodiment of the method, copper nitrate introduced into the chamber via the reactant carrier for producing nitrogen dioxide as calibration fluid is heated by the heater. The use of copper nitrate has the advantage that, in order to produce nitrogen dioxide, copper nitrate has only to be heated, without the addition of further substances, preferably to 180° C. at normal pressure.

According to an advantageous further development of the method, the method is repeated with different reactant carriers having different amounts of first reactant. This has the advantage that the calibration of the respiratory gas analysis device can be checked over a wide measuring range and adjusted where necessary.

BRIEF DESCRIPTION OF THE DRAWINGS

Exemplary embodiments of the disclosure are shown schematically in the drawings and explained in greater detail in the following description. For the elements shown in the various figures and having similar actions, the same reference numerals are used, wherein a repeated description of the elements is not made.

In the figures

FIG. 6 is a flow diagram relating to an exemplary embodiment of the method according to the disclosure.

DETAILED DESCRIPTION

Figure 1:
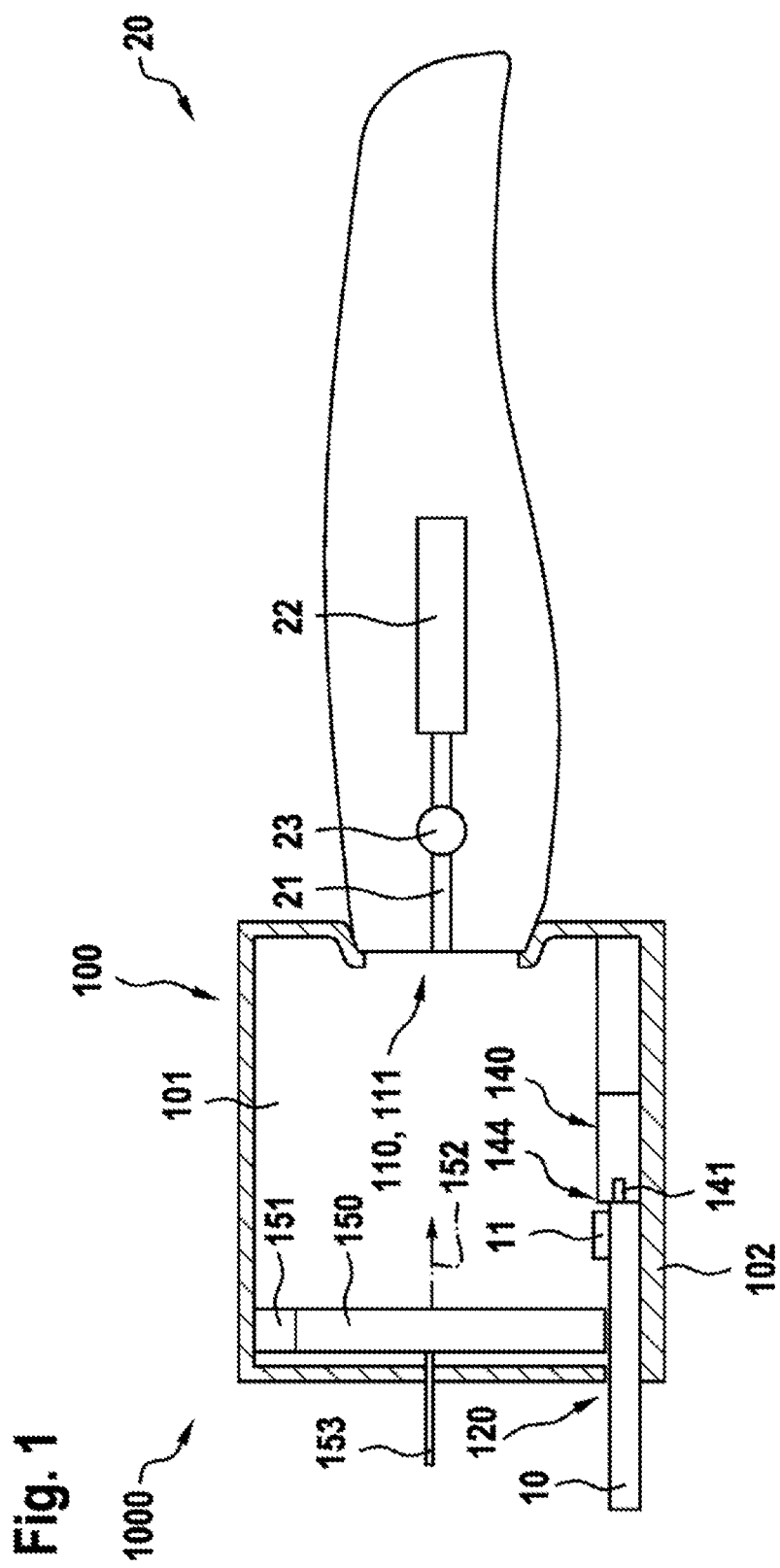
FIGS. 1 to 4 show schematic representations of exemplary embodiments of the system according to the disclosure and of the device according to the disclosure.

FIG. 1 shows an exemplary embodiment of a system 1000 according to the disclosure comprising an exemplary embodiment of a device 100 according to the disclosure for providing a calibration fluid, in particular a nitrogen oxide, for the calibration of a respiratory gas analysis device 20.

The device 100 comprises a first interface 110 for connecting a chamber 101 of the device 100 to a measurement path 21 of the respiratory gas analysis device 20. The device 100 further comprises a first opening 120 for introducing a reactant carrier 10 having a first reactant 11 into the chamber 101, and a contact element 140. The contact element 140 is so arranged in the chamber 101 relative to the first opening 120 that, when the reactant carrier 10 is introduced, contact of the contact element 140 with the reactant carrier 10 for initiating a chemical reaction of the first reactant 11 to produce the calibration fluid is made possible.

The chamber 101 can thereby have a volume, that is to say a capacity for the calibration fluid, of, for example, 500 milliliters. For example, the chamber 101 has a cylindrical shape with a radius of 6 or 5 centimeters and a height of 4.4 or 6.4 centimeters. Alternatively, the chamber 101 can have a cuboid shape with a base area of, for example, 7 by 7 centimeters or 8 by 8 centimeters and a height of 10.2 or 7.8 centimeters. The walls of the chamber 101 can comprise a heat-resistant plastics material, for example polyether ether ketone (PEEK), polyphenylene sulfide (PPS) and/or polytetrafluoro-ethylene (PTFE). Alternatively or in addition, the chamber 101 can also comprise a coating which delimits the volume of the chamber 101, for providing heat resistance relative to the chemical reaction, for example likewise PEEK, PPS and/or PTFE. For an additional cooling function, the walls of the chamber 101 can comprise cooling ribs or fluid channels for a cooling fluid, for example air.

As is shown in FIG. 1, the first opening 120 can in particular be in the form of a slot for the introduction of a reactant carrier 10 in strip form. Preferably, the first opening 120 can be closed when no reactant carrier 10 is introduced, for example via a flap.

Figure 5:
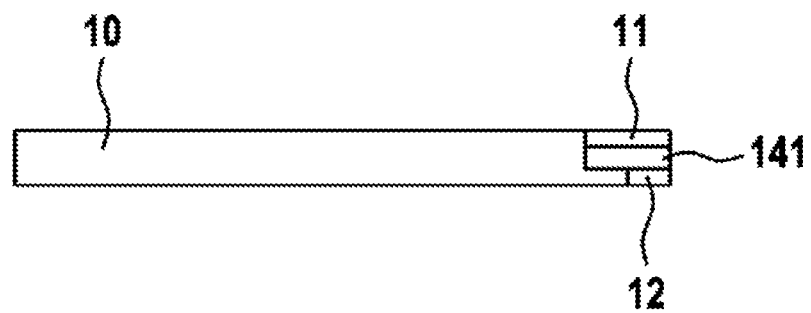
FIG. 5 shows a schematic representation of an exemplary embodiment of the reactant carrier according to the disclosure.

The reactant carrier 10, as is also shown in FIG. 5, is in strip form, for example like a test strip known from medical technology. In this example it comprises a carrier material, for example of plastics material, to one end of which the first reactant 11 is applied, for example, as shown, in a depression. For example, the strip has a length of 50 millimeters, a width of 5 mm and a height of 1 millimeter. Preferably, the dimensions of the first opening 120 are adapted to that width and height.

Figure 2:
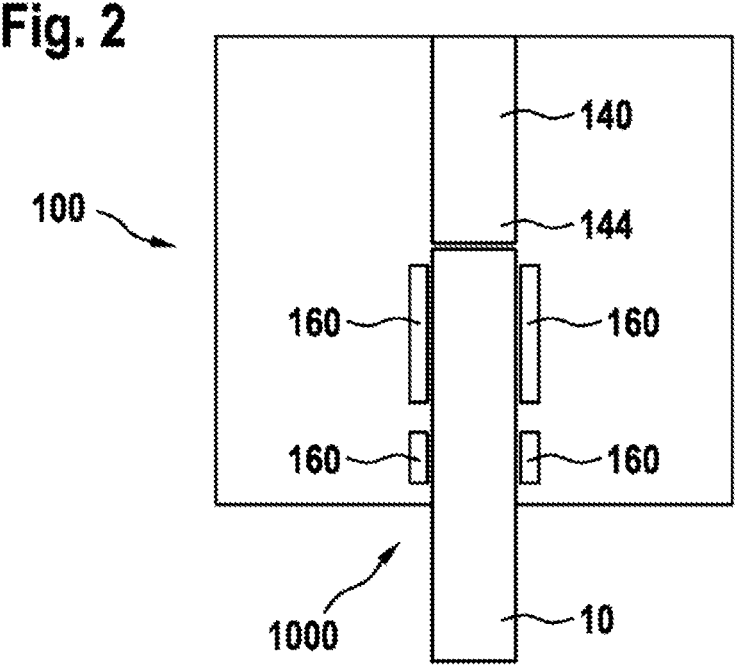

FIG. 1 further shows that the contact element 140 comprises a structure in the form of a projection 144 as a limit for the insertion of the reactant carrier 10. For example, the projection 144 has the same width as the reactant carrier 10. FIG. 2 shows a plan view of the contact element 140 and the reactant carrier 10, from which it is apparent that the contact element 140 comprises further structures 160, in particular walls or projections for fixing the reactant carrier 10 in the chamber 101. As shown, these structures 160 can thereby enclose the reactant carrier 10 at least in part in a U-shape, in order to prevent lateral movement of the reactant carrier 10 relative to the first opening 120. For example, the structures have a thickness of a few millimeters and a height comparable to the reactant carrier 10 of a few millimeters. The structures 144, 160 can comprise the same plastics materials as the walls of the chamber 101 and be integrally formed, for example, with a wall 102 of the chamber 101.

In this exemplary embodiment, the contact element 140 further comprises a heater 141 for heating a portion of the reactant carrier 10, in particular the portion that comprises the first reactant 11. The heater 141 can be, for example, a resistance heater. In particular, the heater can be a DSC chip known from DE 10 2009 056 338 A1. Alternatively, it is also possible for the reactant carrier 10 to comprise the heater 141, as shown in FIG. 5. The heater 141 is thereby arranged beneath the first reactant 11.

The first reactant can be, for example, copper nitrate ($(Cu(NO_3)_2)$) in solid form, which decomposes by heating to, for example, 180° C. to copper oxide, oxygen and nitrogen dioxide. The nitrogen dioxide thereby produced forms the calibration fluid in this example. Nitrogen monoxide is present in respiratory air in a concentration of not more than approximately 200 ppb (parts per billion). For the calibration or checking of the calibration of the respiratory gas analysis device 20, which in this example is based on the device disclosed in EP 1384069 B1, a similar concentration must be provided in order to be able to perform a measurement in the actual measuring range. In order to be able to carry out an interpolation (not an extrapolation) for determining a calibration curve, there is to be provided for the checking preferably nitrogen dioxide in a concentration of 200 ppb, that is to say at the upper edge of the measuring range of the gas sensor of the respiratory gas analysis device 20. As described above, the volume of the chamber 101 is, for example, 500 milliliters. It is assumed for the sake of simplicity that this volume is filled with air. The required copper nitrate layer thickness for a base area of 1 square millimeter can then be estimated as follows. 1 mole of air corresponds to $6.022*10^{23}$ particles and a volume of 22.4 liters. 500 milliliters of air thus correspond to $1.34*10^{22}$ particles. As described above, 200 ppb thereof should be nitrogen dioxide, which in turn corresponds to $2.69*10^{15}$ particles or $4.46*10^{-9}$ moles. 1 mole of copper nitrate yields 2 moles of nitrogen dioxide when heated to 180° C. Thus, in order to be able to produce $4.46*10^{-9}$ moles of nitrogen dioxide, $2.23*10^{-9}$ moles of copper nitrate are required. The molar mass of copper nitrate is 187.5558 grams per mole. $2.23*10^{-9}$ moles of copper nitrate accordingly correspond to $4.19*10^{-7}$ grams. With a density of 3.05 grams per cubic centimeter, this gives a volume of $1.37*10^{-7}$ cubic centimeters. In the case of the base area of 1 square millimeter assumed above, this gives a layer thickness of $1.37*10^{-5}$ centimeters, that is to say 0.137 micrometers.

The layer thickness of the first reactant 11, in particular copper nitrate as described above, can be varied in order to provide calibration fluid, in particular calibration gas comprising nitrogen dioxide, in different concentrations. For example, different reactant carriers 10 with different amounts of first reactant 11 can be used in order to check the calibration of the sensor of the respiratory gas analysis device 20 over a wide measuring range and adjust it where necessary.

As is further shown in FIG. 1, the first interface 110 is in the form of a partially interlocking connection for as tight as possible a connection with the respiratory gas analysis device 20. The first interface 110 thereby comprises a second opening 111 which can preferably be closed, for example via a flap. Fluid present in the chamber 101, in particular the calibration fluid which has been produced, can thus enter the measurement path 21 of the respiratory gas analysis device 20 via the second opening. Preferably, the respiratory gas analysis device 20 comprises a pump 23 arranged in the measurement path 21, which pump is adapted to draw the fluid over the measurement path 21 by suction and convey it further into the measuring chamber 22 in which the gas sensor 24 of the respiratory gas analysis device 20 is located.

The device 100 further comprises a movable piston 150 or plunger 150, called a plunger 150 hereinbelow, for displacing the calibration fluid which has been produced into the measurement path 21 via the second opening 111. The plunger 150 has a surface which completely fills a cross-sectional surface of the chamber 101, which in this example is cuboid-shaped, transversely to a longitudinal axis 152 along which the plunger 150 is movable. The movement of the plunger can preferably take place via an electric drive 151, for example via an electric motor. Alternatively or in addition, the device 100 can comprise a slider 153 which is operable from outside the device 100 and which is connected to the plunger 150 and can be used by an operator to move the plunger 150. A wall 102 of the chamber 101 can thereby comprise a recess for receiving the reactant carrier 10 and the contact element 140 adjoining the reactant carrier in a flush manner, so that the plunger 150 can be moved over the reactant carrier 10 and the contact element 140 for the displacement via the first interface 110 of the calibration fluid which has been produced. Alternatively, the plunger 150 can have a recess adapted to the dimensions of the reactant carrier 10 and of the contact element 140.

Figure 3:
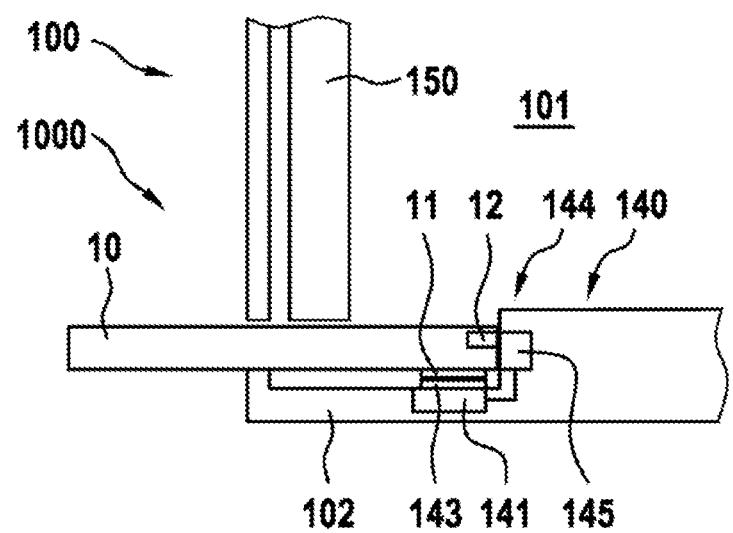

FIG. 3 shows a further exemplary embodiment of the system 1000 according to the disclosure and of the device 100 according to the disclosure. It differs from the exemplary embodiment according to FIG. 1 in that the heater 141 of the contact element 140 is arranged in a wall 102, in this example in the base 102, of the chamber 101 in such a manner that, when the reactant carrier 10 is inserted as far as the projection 144, protruding from the wall, of the contact element 140, the heater is located to the side of the end of the reactant carrier 10 that has the first reactant 11. In this example, a second reactant 143 is arranged on the heater 141, so that the first reactant 11 and the second reactant 143 can come into contact. In this exemplary embodiment, the two reactants can be reactants which, when they react chemically with one another, release the calibration fluid, in particular a nitrogen oxide such as, for example, nitrogen dioxide. Advantageously, the heater 141 can thereby assist the reaction by heating in particular the second reactant 143. The first reactant can be, for example, iron(II) sulfate and the second reactant can be a mixture of sodium bromide and sodium nitrite, which in a chemical reaction with one another produce a gas mixture comprising approximately 98.8% nitrogen monoxide and approximately 1.2% nitrogen.

In an alternative embodiment, a second reactant 143 is not arranged on the heater 141 and the heater 141 can effect heating of the first reactant 11 in order to produce the calibration fluid, for example heating of copper nitrate in order to produce nitrogen dioxide.

In a further alternative embodiment, a heater 141 is not arranged beneath the second reactant 143. This is advantageous in particular when external heat is not required for the chemical reaction of the two reactants 11, 143.

In the device 100 shown in FIG. 3, the contact element 140 further comprises an electrical conducting contact surface 145 for electrical contact with the reactant carrier 10 which has been introduced. The device 100 can be adapted to detect via the electrical contact the presence of a reactant carrier 10 which has been introduced into the device. To that end, the reactant carrier 10 preferably likewise comprises an electrical conducting contact surface 12 or an electrical contact element 12, as shown in FIG. 5. The device 100 can further be adapted, in the case of such a detection, to effect an activation for producing the calibration gas, for example via an activation of the heater 141 of the contact element 140. For example, the contact element 140 can also be adapted, via the electrical contacting of the reactant carrier 10 with the contact surface of the contact element, to close a current circuit for supplying current to the heater 141.

When the reactant carrier 10 comprises the heater 141, the electrical contact surface 12, or the electrical contact element 12, can be connected as shown in FIG. 5 to the heater 141. The reactant carrier 10 can thereby be adapted to start the heater 141 in the case of electrical contact via the contact surface 12, that is to say when an electric potential or a current is applied via the contact surface 12. Preferably, the electrical contact can take place via the above-described electrical contact surface 145 of the contact element 140.

Figure 4:
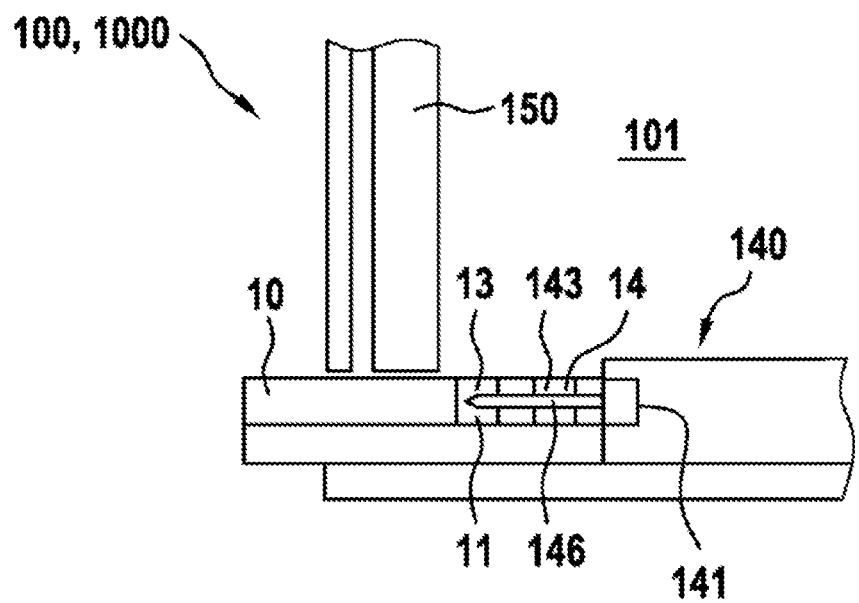

FIG. 4 shows a further exemplary embodiment of the system 1000 according to the disclosure and of the device 100 according to the disclosure. It differs from the exemplary embodiments according to FIG. 1 and FIG. 3 in that the contact element 140 comprises an opening element 146 in the form of a pin 146 or a needle 146. The opening element 146 can, as shown, preferably be so oriented relative to the first opening 120 that, when the reactant carrier 10 is introduced via the first opening 120 into the chamber, the opening element 146 effects the opening of one or more containers 13, 14 of the reactant carrier 10. As can be seen in FIG. 4, a pointed end of the pin 146 or the needle 146 extends in the direction towards the first opening 120. Accordingly, when a user of the device 100 inserts the reactant carrier 10 into the first opening 120, he also effects opening of the containers 13, 14 of the reactant carrier at the same time. In this example, the reactant carrier comprises a first container 13 having the first reactant 11 and a second container 14 having the second reactant 143, which containers are pierced in succession by the opening element 146 on insertion. The two reactants 11, 143 are thus able to escape from the containers 13, 14 and mix for the subsequent chemical reaction to produce the calibration fluid. This embodiment of the disclosure is thus advantageous in particular for liquid reactants 11, 143.

FIG. 6 shows a flow diagram for an exemplary embodiment of the method 500 according to the disclosure for calibrating a respiratory gas analysis device. The method 500 can be carried out with one of the above-mentioned exemplary embodiments of the system 1000 according to the disclosure and of the device 100 according to the disclosure. In a first step 501, the respiratory gas analysis device 20 is connected to the device 100 for providing a calibration fluid, wherein the connection of the respiratory gas analysis device 20 to the device 100 takes place via the first interface of the device 100. In a second step 502, a reactant carrier 10 having the first reactant 11 is introduced into the chamber 101 of the device 100. Alternatively, the second step 502 can also be carried out before the first step 501. In a third step 503, the calibration fluid, in particular comprising one or more different nitrogen oxides, is produced in the chamber 101 via a chemical reaction involving at least the first reactant 11. In a fourth step 504, the calibration fluid is introduced into the measurement path 21 of the respiratory gas analysis device 20 for calibration of the respiratory gas analysis device 20, and the calibration is carried out.

Preferably, the introduction of the calibration fluid into the measurement path 21 is assisted by suction by means of the pump 23 of the respiratory gas analysis device 20. According to an advantageous further development of the method, at least a portion of the reactant carrier 10 which comprises the first reactant 11 is heated via the heater 141 of the device 100 to a reaction temperature. In particular, the first reactant 11, as described above, can be copper nitrate and heating can thus take place preferably to at least 180° C.

The invention claimed is:

1. A device for providing a calibration fluid for calibration of a respiratory gas analysis device, comprising:
    a first interface configured to connect a chamber of the device to a measurement path of the respiratory gas analysis device;
    a first opening configured to receive into the chamber a reactant carrier structure, on or in which a first reactant is disposed; and
    a contact element comprising an electrical conducting contact surface, the contact element arranged in the chamber relative to the first opening in such a way that, when the reactant carrier structure is introduced into the first opening, the electrical conducting contact surface electrically contacts the reactant carrier structure so as to initiate a chemical reaction of the first reactant to produce the calibration fluid.

2. The device as claimed in claim 1, wherein the contact element further comprises a projection structure configured to contact the reactant carrier structure when the reactant carrier structure has been introduced into the chamber.

3. The device as claimed in claim 2, wherein the projection structure is configured to fix the reactant carrier structure in the chamber.

4. The device as claimed in claim 1, further comprising:
    a movable piston or plunger configured to displace the calibration fluid through the first interface.

5. The device as claimed in claim 1, wherein the contact element further comprises a heater configured to heat the first reactant to a specified reaction temperature.

6. The device as claimed in claim 5, wherein the electrical conducting contact surface is configured to electrically contact the heater so as to activate the heater to heat the first reactant to the specified reaction temperature.

7. The device as claimed in claim 1, wherein the contact element further comprises a second reactant.

8. The device as claimed in claim 1, wherein the contact element comprises an opening element configured to open a container of the reactant carrier structure to release at least one of the first reactant and a second reactant from the container.

9. The device as claimed in claim 8, wherein the opening element is a pin or a projection.

10. The device as claimed in claim 1, wherein the device is further configured to electrically charge an energy store of the respiratory gas analysis device.

11. The device as claimed in claim 1, wherein the calibration fluid is a nitrogen oxide.

12. A system for providing a calibration fluid for calibration of a respiratory gas analysis device, comprising:
    a reactant carrier structure on or in which a first reactant for the chemical production of the calibration fluid is disposed; and
    a device comprising:
        a first interface configured to connect a chamber of the device to a measurement path of the respiratory gas analysis device;
        a first opening configured to receive the reactant carrier structure into the chamber; and
        a contact element comprising an electrical conducting contact surface, the contact element arranged in the chamber relative to the first opening in such a way that, when the reactant carrier structure is introduced into the first opening, the electrical conducting contact surface electrically contacts the reactant carrier structure so as to initiate a chemical reaction of the first reactant to produce the calibration fluid.

13. The system as claimed in claim 12, wherein the reactant carrier structure further comprises a heater or a microsystem heater arranged beneath the first reactant in such a way that the electrical contact between electrical conducting contact surface and the reactant carrier structure activates the heater to heat the first reactant to the specified reaction temperature.

14. A method for calibrating a respiratory gas analysis device, comprising:
   connecting the respiratory gas analysis device to a device for providing a calibration fluid via a first interface of the device;
   introducing a reactant carrier structure on or in which a first reactant is disposed into a chamber of the device in such a way that an electrical conducting contact surface of a contact element of the device electrically contacts the reactant carrier structure;
   as a result of the electrical contact, initiating production of the calibration fluid via a chemical reaction of the first reactant in the chamber; and
   introducing the calibration fluid into a measurement path of the respiratory gas analysis device and carrying out the calibration of the respiratory gas analysis device.

15. The method as claimed in claim 14, wherein the introduction of the calibration fluid into the measurement path is assisted by suction of a pump of the respiratory gas analysis device.

16. The method as claimed in claim 14, the initiating of the production of the calibration fluid including, as a result of the electrical contact, heating at least a portion of the reactant carrier structure to a reaction temperature via a heater of the device.

17. A method for calibrating a respiratory gas analysis device, comprising:
   connecting the respiratory gas analysis device to a device for providing a calibration fluid, wherein the respiratory gas analysis device is connected to the device via a first interface of the device;
   introducing a reactant carrier having a first reactant into a chamber of the device i;
   heating at least a portion of the reactant carrier to a reaction temperature via a heater of the device;
   producing the calibration fluid via a chemical reaction of the first reactant in the chamber; and
   introducing the calibration fluid into a measurement path of the respiratory gas analysis device and carrying out the calibration of the respiratory gas analysis device, wherein:
   the introducing of the reactant carrier includes introducing copper nitrate into the reaction chamber via the reactant carrier as the first reactant, and
   the heating of at least the portion of the reactant carrier includes heating the copper nitrate with the heater to produce nitrogen dioxide as the calibration gas.

* * * * *